United States Patent [19]

Lee

[11] Patent Number: 4,971,075
[45] Date of Patent: Nov. 20, 1990

[54] SURGICAL KIT AND METHOD FOR TENDON REPAIR

[76] Inventor: Hans Lee, Ste. 200, 415 Morris St., Charleston, W. Va. 25301

[21] Appl. No.: 437,960

[22] Filed: Nov. 17, 1989

[51] Int. Cl.$^5$ ............................................. A61B 11/00
[52] U.S. Cl. ..................................... 128/898; 606/224
[58] Field of Search .......................... 128/898, 334 R; 606/152, 216, 224

[56] References Cited

U.S. PATENT DOCUMENTS 4,781,190  1/1988  Lee ..................................... 606/139

OTHER PUBLICATIONS

Tonkin, Michael et al, "Flexor Tendon Surgery-Today and Looking Ahead", Perspectives in Hand Surgery, vol. 13:2, pp. 221-241 (4/1986).
Ketchum, Lynn D., "Suture Material and Suture Techniques Used in Tendon Repair", Hand Clinics, vol. 1, No., (2/1985).
Strickland, James W., "Flexor Tendon Repair", Hand Clinics, vol. 1, No. 1, Feb. 1985.
"The 'Grasping' Technique for Tendon Repair", by Kessler, 1973, Surgical Techniques in Early Flexor Tendon Repairs, Including Early Motion (Panel Discussion).
"Symposium on Tendon Surgery in the Hand", Philadelphia, PA, Mar. 1974.
"Tendon Surgery in the Hand", The C.V. Mosby Company, 1987.
"Operative Hand Surgery", Churchill Livingstone, 1988.
"Intra-Tendinous Tendon Suture in the Hand", Kenya Tsuge et al, The Hand-vol. 7, No. 3, 1975.

Primary Examiner—Randall L. Green
Assistant Examiner—Gary Jackson
Attorney, Agent, or Firm—Lowe, Price, LeBlanc, Becker & Shur

[57] ABSTRACT

A method and kit for tendon repair and two variations thereof using double loop locking sutures in disclosed. A pair of loop locking sutures are formed in each tendon end. The needle of each loop locking suture extends through the tendon fiber out of the tendon end for securement to the corresponding loop locking sutures formed in the other tendon end. The loop locking sutures transfer tensile loading along the axis of the tendons into transverse compression loads through the loop locking sutures. In one variation, the double loop locking sutures connect tendons of different diameter together. In a second variation, the tendon is attached to bone.

11 Claims, 7 Drawing Sheets

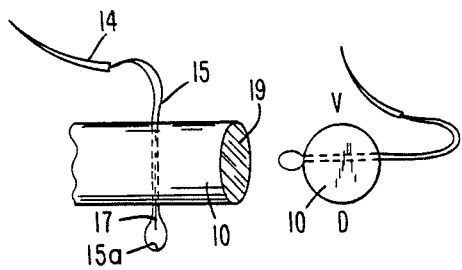
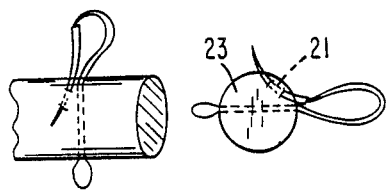
FIG. 1  FIG. 1a  FIG. 2  FIG. 2a
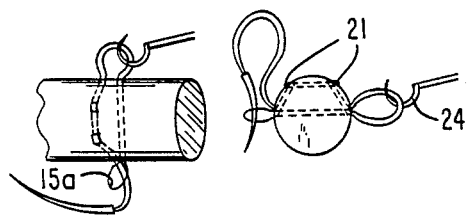
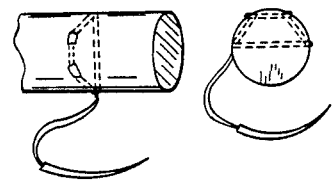
FIG. 3  FIG. 3a  FIG. 4  FIG. 4a
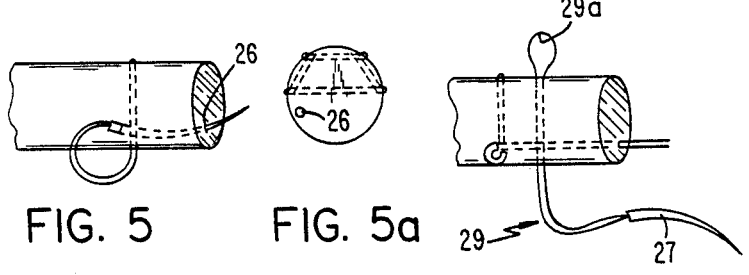
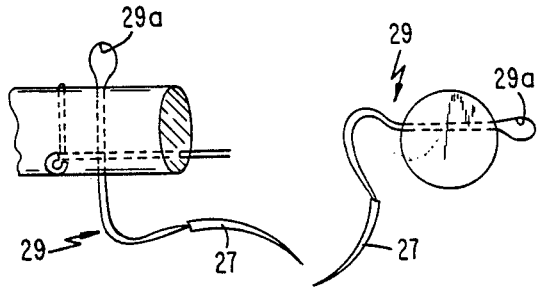
FIG. 5  FIG. 5a  FIG. 6  FIG. 6a
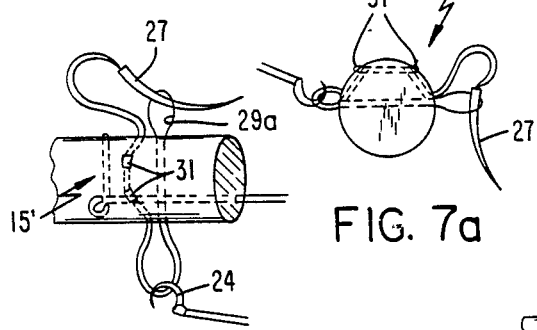
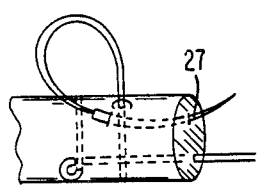
FIG. 7  FIG. 7a  FIG. 8  FIG. 8a

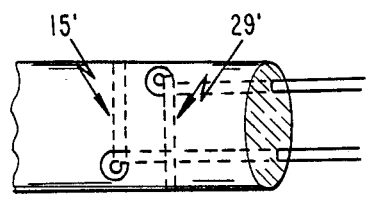 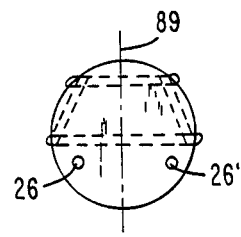
FIG. 9  FIG. 9a
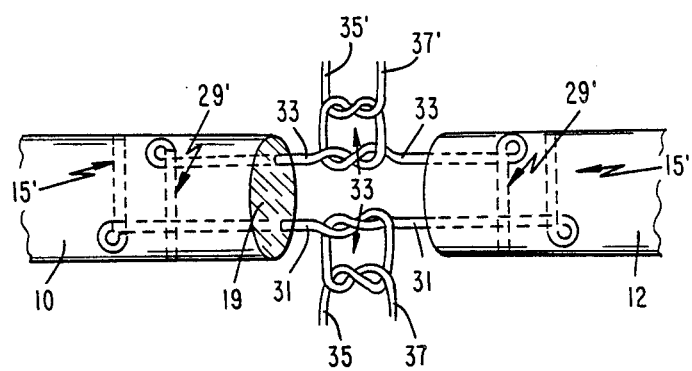
FIG. 10
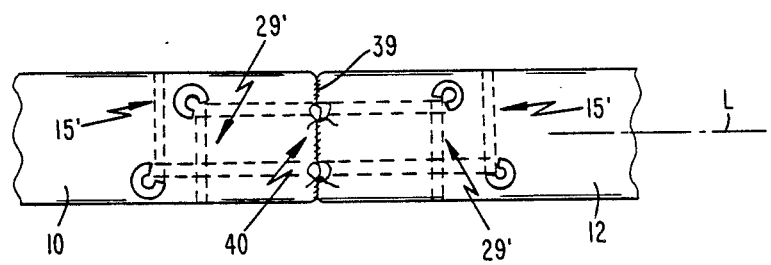
FIG. 11

SURGICAL KIT AND METHOD FOR TENDON REPAIR

TECHNICAL FIELD

The present invention relates to surgical kits and techniques for tendon repair for early active mobilization, and more particularly, to a double loop locking suture tendon repair technique involving the transfer of longitudinal loads through a repaired tendon juncture into transverse compression forces by the use of double loop locking sutures.

BACKGROUND ART

Notwithstanding the advances in tendon surgery during the past half century, a significant number of patients with flexor tendon injuries do not regain satisfactory functions. Such injuries result in severe functional loss from adhesion of repaired tendons, stiffness and flexion contracture of the fingers.

The principal theory for base-of-tendon healing has been the extrinsic mechanism by synovial sheath, parisheath, and migration of fibroblasts, although a number of researchers have reported strong evidence supporting the intrinsic healing mechanism by tenocytes and tenoblasts. Other studies show that the healing of immobilized tendon repair begins with the extrinsic mechanism followed by the intrinsic mechanism.

There is ongoing controversy about whether the repaired tendon should be immobilized completely, partially, or not at all. A number of studies have shown that actively mobilized tendon repair can heal with less or no restraining adhesion followed by satisfactory functional recovery. However, a common drawback of currently popular techniques of tendon repair of which I am aware is that they do not provide enough tensile strength with safety margins for early active mobilization. When a tendon is repaired with any of these techniques, immediate active mobilization will likely separate the tendon juncture as a result of elongation of the suture frame, breakdown of the sutures or pull through of the sutures.

Accordingly, there exists an unfulfilled need in modern hand surgery for a tendon repair technique with sufficient tensile strength and safety margin to enable early active mobilization likely to discourage stiff joints, adhesion and flexion contracture while enhancing the intrinsic healing mechanism aided by synovial diffusion.

SUMMARY OF THE INVENTION

It is accordingly one object of the present invention to provide a tendon repair technique and kit therefor such that the sutured tendon juncture has sufficient tensile strength with safety margin to allow for early active mobilization so as to discourage stiff joints, adhesion and flexion contracture and to aid the intrinsic healing mechanism.

Another object of the invention is to provide a tendon repair technique and kit wherein the principle of repair involves the transfer of longitudinal loading through the tendon juncture into transverse compression forces acting on opposite sides of the juncture through the use of double loop locking sutures.

Still a further object of the invention is to provide a tendon repair technique and kit utilizing looped sutures that avoid gap formation which is a well known cause of adhesion.

Still another object of the present invention is to provide a tendon repair technique and kit for connecting tendons of the same diameter, different diameters (e.g., tendon graft) or for tendon insertion into bone for tendon graft and transfer.

Another object of the present invention is to provide a tendon repair surgical kit containing appropriate surgical needles and looped sutures with instructions for preferred use in reconstructive tendon repair surgery.

A method of tendon repair, in accordance with the present invention, comprising the steps of inserting a needle of a first loop suture across a mid-axis of a tendon end and then taking one or plural superficial stitches along the volar half of the tendon so as to return the needle to the loop remaining at the entry point. The needle is then passed through the loop and the suture is tightened to establish a first loop locking or lock-up suture in the volar half of the tendon. The needle is then inserted along the tendon fiber, under and across the lockup suture and out through the end of the tendon. A needle of a second loop suture is then inserted across the mid-axis of the tendon in diametrically opposed location from the entry point of the first suture and spaced a predetermined distance from the first suture in the direction of the tendon end. A second loop locking or lockup suture is then formed in the volar half of the tendon in identical to the first lockup suture and the needle is then inserted along the tendon fibers, under and across the second lockup suture out through the end of the tendon in symmetric spaced relationship from the exit point of the first needle. A pair of first and second loop sutures are formed in the second tendon in a manner identical to the first and second lockup loop sutures in the first tendon. Thereupon, the ends of the first sutures in each tendon and the ends of the second sutures in each tendon projecting from the tendon ends are knotted together, preferably with a square knot, enabling the sutures to be snugged with the tendon ends abutting against each other without a gap or buckling. The tendon juncture may then be approximated with a running or horizontal mattress preferably utilizing a nonabsorbable suture.

The foregoing surgical technique can also be used for suturing tendons of different diameter. In accordance with this technique, a pair of loop sutures are formed in the ends of each tendon in the manner set forth above, except that the larger diameter tendon is split with the first and second lockup loop sutures formed in a portion of the tendon end located adjacent the apex of the split and with the sutures extending from the end of the split tendon through an apex thereof. Both pairs of sutures are knotted together in the manner described above and between the split and the sutures are snugged so that the smaller diameter tendon end enters and is maintained between the split ends of the larger diameter tendon. Intussusception is completed by running sutures along the split margins with the running sutures catching a few tendon fibers of the smaller diameter tendon at every other bite.

A technique for grafting tendon to a bone is also disclosed. After forming the first and second lockup loop sutures in the end of the tendon in the manner described in connection with the first embodiment, the needles of the first and second lockup loop sutures are inserted through the cortical window until the suture end of the needle is right on the cortex. As the needle end touches the lateral surface of the cortex (not in the window), the needle is tilted volarward and slid along the cortex until it appears in the wound. Both pairs of sutures are then tied together with the distal excess of the tendon removed and the stump of the tendon gently pushed into the cortical window.

As a result of extensive experimentation, the highest tensile strength was achieved with a nonabsorbable, multifilament loop suture wherein opposite ends of the loop are swaged into a curved needle preferably having a reverse cutting tip. The loop suture preferred material is usually 4-0, and occasionally 3-0 or 5-0 Nylon (e.g., Supramid ®) or polyester (e.g., Dacron).

Still other objects and advantages of the present invention will become readily apparent to those skilled in this art from the following detailed description, wherein only the preferred embodiments of the invention are shown and described, simply by way of illustration of the best mode contemplated of carrying out the invention. As will be realized, the invention is capable of other and different embodiments, and its several details are capable of modifications in various obvious respects, all without departing from the invention. Accordingly, the drawing and description are to be regarded as illustrative in nature, and not as restrictive.

BRIEF DESCRIPTION OF DRAWINGS

FIGS. 1-9 are perspective views of a tendon end sequentially depicting the manner of forming a pair of lockup loop sutures in accordance with the present invention and FIGS. 1A-9A are sectional views depicting a cross-sectional illustration of the loop lockup suture respectively formed in accordance with FIGS. 1-9;

FIG. 10 is a perspective view depicting the preferred method for securing the tendon ends together with the double loop lockup sutures formed in each tendon end;

FIG. 11 is a partly sectional and partly schematic view depicting the repaired tendon ends sutured together using the procedure of the present invention;

BEST MODE FOR CARRYING OUT THE INVENTION

Figure 12:
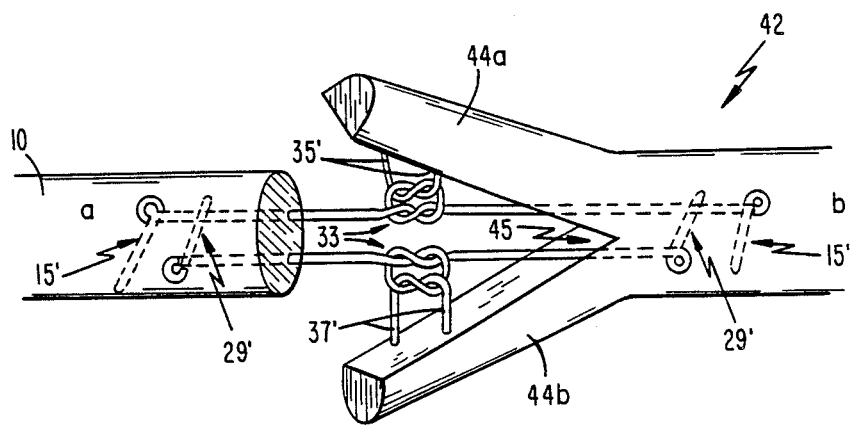
FIG. 12 is a perspective view of an alternate technique for securing a small diameter and large diameter tendon end together.

FIGS. 1-11 are illustrations of a novel surgical technique, in accordance with the present invention, for end-to-end repair of first and second tendons 10 and 12 of a severed tendon, of approximately the same diameter. As will be seen more fully below, the principle of repair in accordance with this invention involves the transfer of the longitudinal load normally acting along the longitudinal axis L of the tendon into a transverse compression force by the use of double loop locking sutures. As a result of extensive experimentation discussed below, the preferred material for the loop sutures is non-absorbable multifilament, usually 4-0, occasionally 3-0 or 5-0, Nylon (e.g., Supramid ®) or polyester (e.g., Dacron ™), depending upon the type of tendon being repaired. The invention preferably utilizes a 1/3 circle needle 14 of 3/8 inch diameter with a loop suture 15 having its opposite free ends conventionally swaged to the needle to define a loop.

With reference to FIGS. 1 and 1A, the needle 14 of the first loop suture 15 is inserted through the tendon 10 across the mid-axis 17 approximately 8-10 mm from the end 19 of the tendon. Next, two or three very superficial bites 21 (one or two for small tendons) are taken through the volar half 23 of the tendon 10 as "purse string" stitches depicted in FIGS. 2, 2A, 3 and 3A. The tip of the needle 14 is then passed through the loop 15a of the first suture 15 and the suture is tightened with the assistance of a blunt hook 24. Thereby, the volar half of the tendon 10 is snugly locked up (FIGS. 4, 4A).

With reference to FIGS. 5 and 5A, the needle 14 is then inserted along and through the tendon fiber 10 by initially inserting the needle into the tendon on the side of the suture 15 located remote from the tendon end 19. The needle 14 and suture material pass under and across the first lockup suture 15' of FIGS. 4, 4A and out through the end 19 of the tendon as at 26; the needle is then pulled to snug up the suture material between the needle and the lockup suture.

A needle 27 of a second loop suture 29 is then inserted across a mid or diametrical axis of the tendon 10 approximately 2 mm from the first lockup suture 15' and closer towards the tendon end 19 so as to locate the second loop 29a of the second loop suture diametrically opposite the first loop of the first loop suture as depicted in FIG. 6. One or two purse string stitches 31 are repeated with the second needle 27 in the volar half of the tendon and the second needle is then passed through the second loop 29a as depicted in FIGS. 6A, 7 and 7A in a manner substantially identical to the first loop suture 15 described above. The second needle 27 is then inserted to run within and along the tendon fiber 10, both under and across the second lockup suture 29' as depicted in FIGS. 8 and 8A following the passing of the second needle through the second loop 29a and tightening of the second lockup suture, assisted with a blunt hook 24, as depicted in FIGS. 8 and 8A, and exits the tendon end as at 26'.

FIGS. 9 and 9A are illustrations of the first tendon 10 with the first and second lockup sutures 15', 29' sewn therein in the manner described above. The first and second needles 14, 27 and a remaining length of each first and second loop suture 15, 29 extends from the end 19 of the first tendon 10.

With reference to FIG. 10, first and second lockup sutures 15', 29' are also formed in the second tendon 12 in a manner identical to the first and second lockup sutures 15', 29' of the first tendon 10 described supra. With reference to FIG. 10, the free ends 35 and 37 of the first lockup sutures 15' of the first and second tendons 10, 12 and the free ends 35', 37' of the second lockup sutures 29' of the first and second tendons are respectively tied together with a square knot 33 which is formed by making an open ended loop with the free end 35 of one of the first lockup sutures 15' and then passing the free end 37 of the first lockup suture of the second tendon 12 through the loop and over, around and under the portion of the first lockup suture 15, extending from the first tendon end 19; the remaining free end 37 of the first lockup suture of the second tendon is then passed over and outside the free end of the first suture material of the first tendon and then back through the open ended loop such that the free ends 35, 37 of the first sutures are parallel to each other as depicted in FIG. 10. The same knotting procedure is utilized with the free ends 35', 37' of the second lockup sutures 29'. The resulting square knots 33 are then tightened to pull the tendon ends 19 into abutting contact with each other without buckling the tendon ends. The knots 33 and thereby the corresponding lockup sutures 15', 15' and 29', 29' are tied four times to snugly secure the sutures with care exercised to avoid buckling the tendon ends. Finally, with reference to FIG. 11, the tendon juncture 39 is approximated with a running or horizontal mattress 40, preferably utilizing 6-0 or 7-0 nonabsorbable suture.

Figure 13:
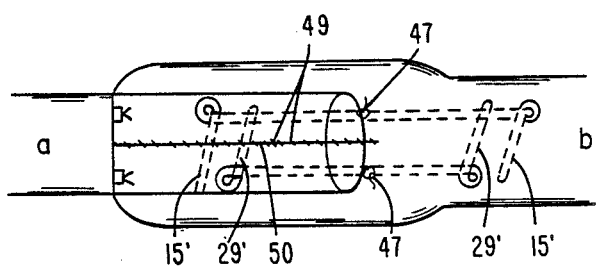
FIG. 13 is a partly sectional and partly schematic view of the repaired tendon ends of FIG. 12.

FIGS. 12 and 13 are illustrations of a variation of the surgical technique set forth in FIGS. 1–11 and is preferred for repairing tendons 10 and 42 of different diameter (e.g., tendon graft). With reference to FIG. 12, the first and second lockup sutures 15', 29' formed in the smaller diameter tendon 10 are identical to the first and second lockup sutures formed in the first tendon of FIGS. 1–11. Likewise, the first and second lockup sutures 15', 29' formed in the second or larger diameter tendon 42 of FIG. 12 are identical to the first and second lockup sutures formed in the second tendon of FIGS. 1–11. However, in the larger diameter tendon 42, the tendon end is split into two halves 44a and 44b and the ends of each first and second lockup suture 15', 29' in the second tendon 42 extend through the tendon from their associated lockup sutures into the split area between the halves through an apex 45 thereof. The resulting four ends of the first and second lockup sutures 15', 15', 29, 29' of the first and second tendons 10, 42 are then respectively secured together utilizing a square knot 33 in the manner described above in connection with the first embodiment of the invention (FIGS. 10 and 11). After forming the square knots 33, the remaining free ends 35, of the first suture (i.e., those portions of the suture connected directly to the surgical needle), and likewise the remaining free ends 37' of the second sutures, extend transversely through one of the split halves 44a, 44b of the larger diameter tendon 42 located outwardly adjacent the knot 33. The square knots 33 and thereby the connected first and second lockup sutures 15', 15', 29', 29' in each tendon 10, 42 are then snugged so that smaller diameter tendon 10 enters between the split halves 44a, 44b of the larger diameter tendon 42. The ends 35', 35', 37', 37' of the first and second sutures extending outwardly from the associated split half of the larger diameter tendon 42 are then secured with a knot 47. The intussusception is then completed by running sutures 49 along the split margins 50. The running sutures 49 preferably catch a few tendon fibers of the small tendon 10 with every other bite. The length of the intussusception is usually 1.5–2 cm and must not encroach on the adjacent pulley (not shown) through which tendons glide for better function as well known to practitioners.

Figure 14A:
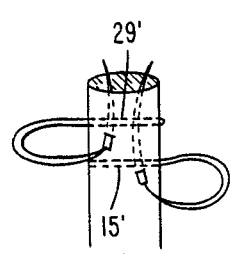
FIGS. 14A-14G are perspective views sequentially depicting a third embodiment of a surgical technique in accordance with the present invention for securing a tendon to bone.
Figure 14B:
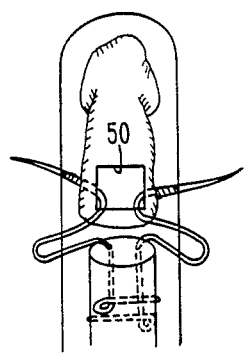
Figure 14C:
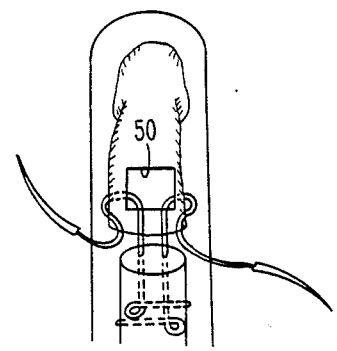
Figure 14D:
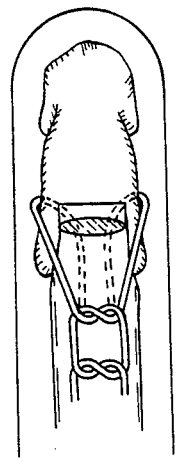
Figure 14E:
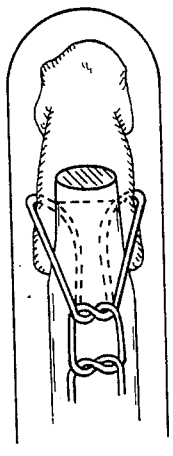
Figure 14F:
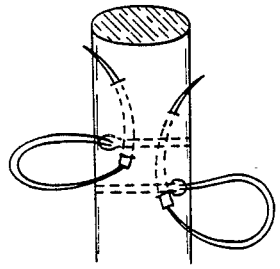
Figure 14G:

FIGS. 14A–14B are illustrations of a third embodiment of the present invention for tendon insertion into bone as may be used in tendon graft and transfer. With reference to FIG. 14A, a pair of double loop lockup sutures 15', 29' are formed in the tendon end in the manner described in connection with the first embodiment of FIGS. 1–9. The needles 14, 27 of each first and second lockup suture 15', 29' are then inserted through the cortical window 50 of the bone and through the lateral hole until the suture end of the needle is right on the cortex. Usually, the needle gets pulled out of the skin and has to be pushed back into the skin by pulling the sutures from the window 50. As the needle end touches the lateral surface of the cortex (not into the window), the needle end is tiltered in the direction of the volar and slide along the cortex until it appears in the wound outside the window frame (FIG. 14C). With reference to FIG. 14D, both pairs of sutures are then pulled until the end of the tendon inserts tightly into the window. Both pairs of sutures are then tied off approximately four or five times. With reference to FIG. 14F, the sutures can exit along the sides of the tendon, especially on a small tendon. After the sutures are tied securely (14E), the distal excess of the tendon is removed (exercising care to avoid damage to the suture) and the stump of the tendon is gently pushed into the cortical window. The tendon is then finally inserted into the cortical window and the suture knots are then finally tightened as depicted in FIG. 14G.

Figures 15, 15A:
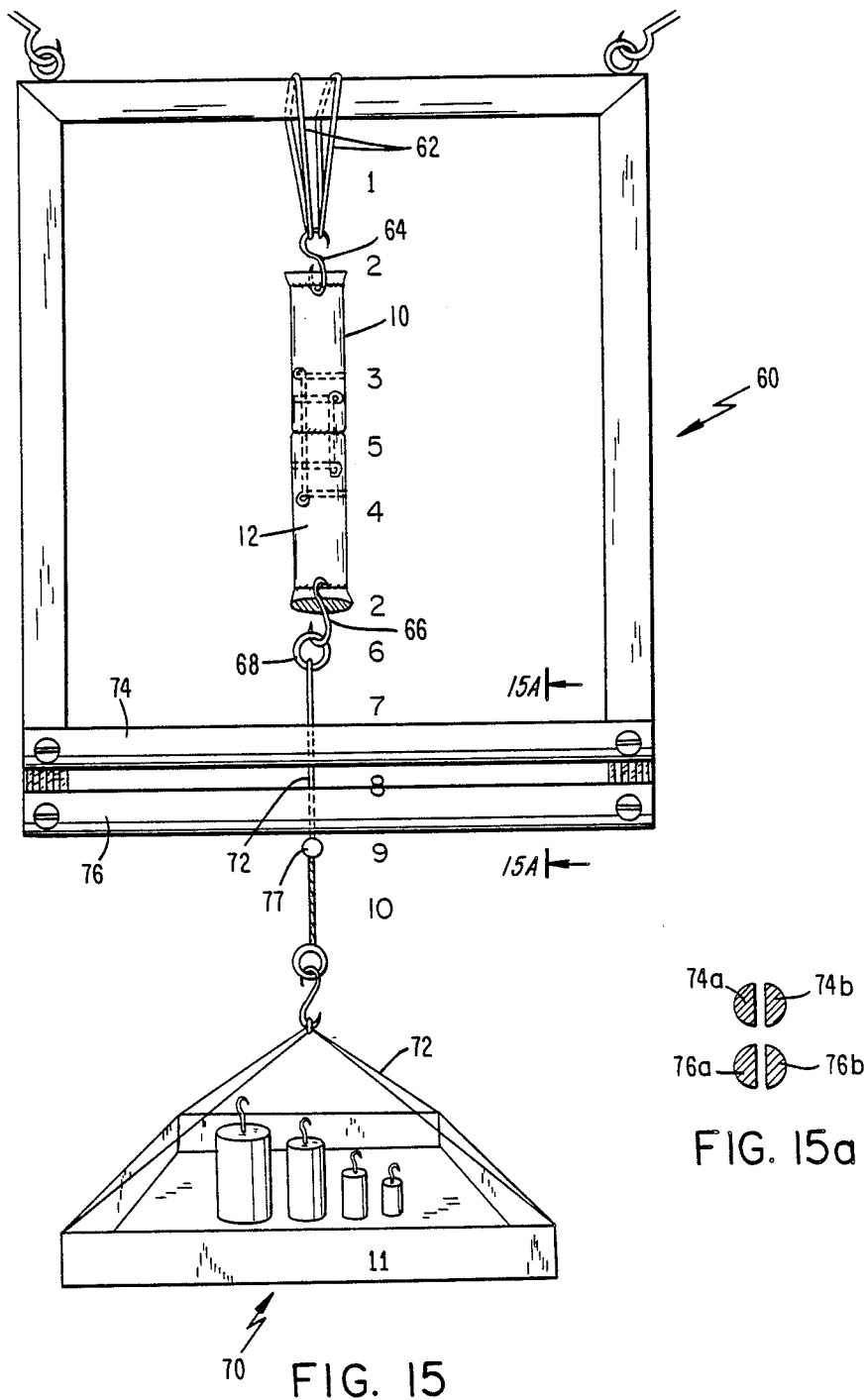
FIG. 15 is a perspective view of an assembly used for testing the tensile strength of a repaired tendon.

FIG. 15 is an illustration of an Experiment I conducted by the inventor where forty tendons were repaired with the double loop locking suture technique in accordance with the present invention and twenty-six tendons were repaired with a known grasping suture technique (Kessler), all using 4-0 Dacron. The repaired tendons 10, 12 were individually suspended on steel frames 60 using a pair of rubber bands (size 8) 62 with the upper end of the first tendon 10 connected to the rubber bands with a hook 64. The lower end of each repaired tendon 12 was connected via a second hook 66 and ring 68 to a weight tray 70 utilizing wire 72 connected to the ring 68 and extending between pairs of vertically spaced horizontal bottom frame members 74 and 76 with each horizontal bottom frame member being formed from two spaced members 74a, 74b, and 76a, 76b with the wire 72 extending therebetween. Each tendon was placed under an initial tension of 1000 grams to maintain the suspended tension of the repaired tendon with 1000 grams of weight is placed on tray 70, a clamp (not shown) is applied on the wires at the space between the two bottom frames 74, 76. The weight is then removed. A stopper (e.g., split lead shot 77) is inserted between the two wires 72, just below the bottom frame 76, the lower part of the two wires below the stopper 77 being twisted tightly; then the clamp is removed. By the gradual addition of incremental weights, the tensile strength (breaking weight) was measured and recorded. After each measurement, the frames with the remaining tendon repairs (maintaining suspension on the frame at 1000 gram tension) were preserved in cool saline. Serial measurements of the tensile strength of the tendon unions were performed at zero, one, two, three, five and eight weeks following repair.

Figure 16:
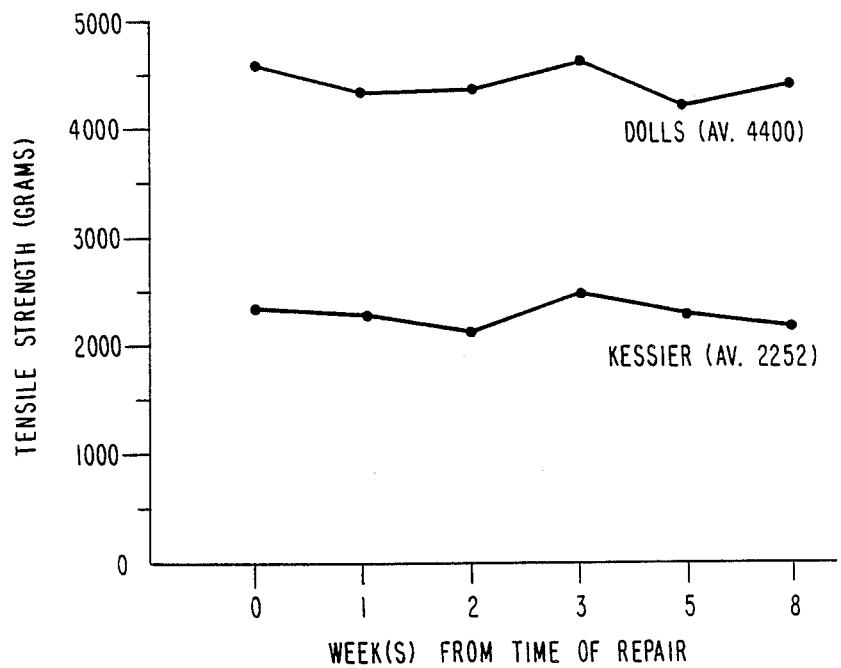
FIG. 16 is a graph depicting the results of the experimentation achieved with the testing frame of FIG. 15.

Table 1 and FIG. 16 depict the result of the aforementioned experiment establishing that the average tensile strength of tendon unions was 4400 grams with the double loop locking suture technique of the present invention and 2252 grams with the known grasping suture technique. Approximately a third of repairs made with the known grasping suture technique developed a gap between the tendon ends of approximately 3 to 4 mm as they were placed under the initial loading tension of 1000 grams. With the double loop locking suture technique of the present invention, gaps were rare. Both repairs maintained their tensile strength throughout the test period of eight weeks. During the measurement, most of the tendon ruptures occurred through the sutures near the knots but there was no rupture at or near the loop portions of the double loop locking suture technique of the present invention.

TABLE 1

Serial Comparison Study of Tensile Strength of Tendon Repair by DOLLS and Grasping Suture (Kessler) Technique

| Week from Repair | 0 W | 1 W | 2 W | 3 W | 5 W | 8 W | TOTAL |
|---|---|---|---|---|---|---|---|
| DOLLS 4-0 Dacron | | | | | | | |
| No. of tendon | 10 | 6 | 6 | 6 | 6 | 6 | 40 |
| average t.s. | 4581 | 4316 | 4324 | 4595 | 4201 | 4384 | 4400 |
| KESSLER 4-0 Dacron | | | | | | | |
| No. of tendon | 6 | 4 | 4 | 4 | 4 | 4 | 26 |
| average t.s. | 2323 | 2285 | 2123 | 2460 | 2268 | 2146 | 2252 | t.s.: tensile strength

TABLE 2

Serial Comparison Study of the Tensile Strength of Double Loop Sutures among Dacron, Ethibond and Supramid

| Week from Repair | 0 | 1 | 2 | 3 | 5 | 8 | TOTAL |
|---|---|---|---|---|---|---|---|
| Dacron (4-0) | | | | | | | |
| No. of suture | 6 | 4 | 4 | 4 | 4 | 4 | 26 |
| Average t.s. | 4112 | 4143 | 4240 | 4293 | 4090 | 4497 | 4229 |
| Ethibond (4-0) | | | | | | | |
| No. of suture | 6 | 4 | 4 | 4 | 4 | 4 | 26 |
| Average t.s. | 3790 | 3890 | 3500 | 3770 | 3743 | 3589 | 3713 |
| Supramid (4-0) | | | | | | | |
| No. of suture | 6 | 4 | 4 | 4 | 4 | 4 | 26 |
| Average t.s. | 4810 | 4793 | 4690 | 4601 | 4883 | 4697 | 4745 | t.s.: tensile strength

Figure 17:
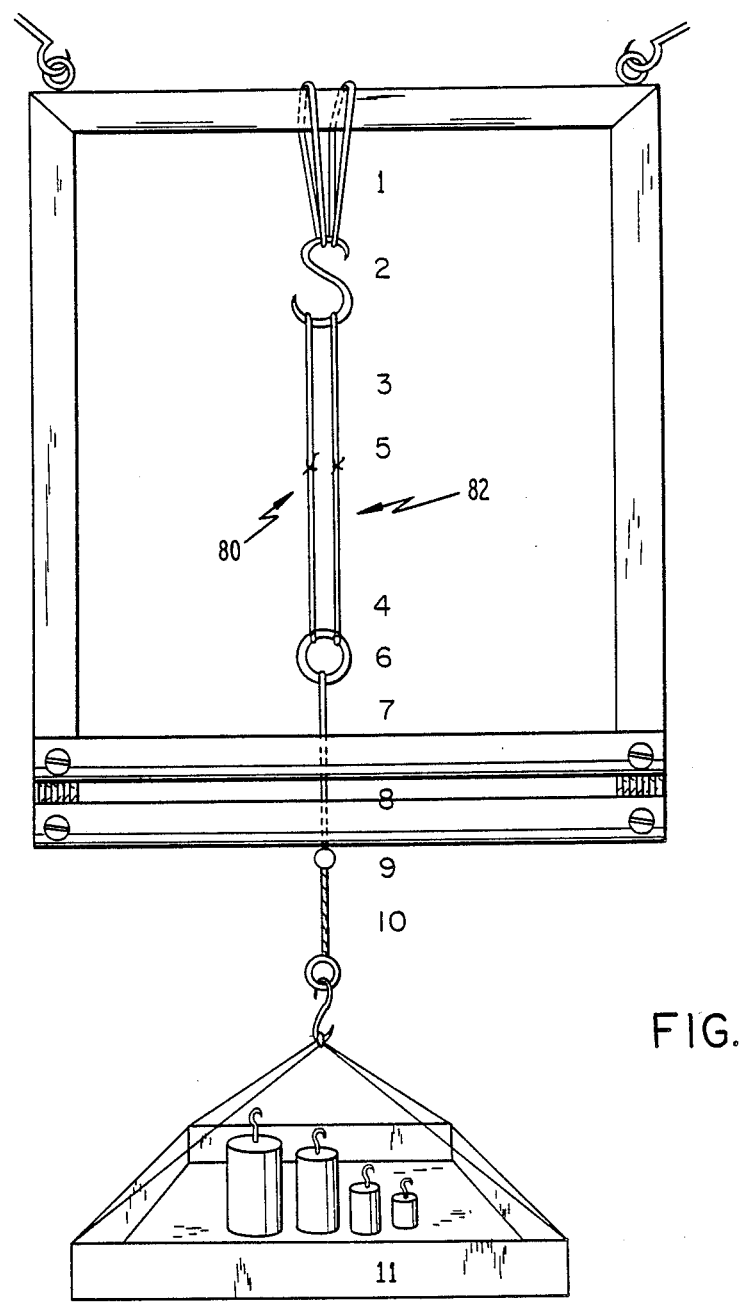
FIG. 17 is another testing frame utilized for conducting the tensile strength test on the double loop locking sutures only.

With reference to FIG. 17, a second experiment was conducted utilizing the same type of stainless steel frame depicted in FIG. 15 wherein a pair of double loop locking sutures (only) were constructed for each unit. In the second experiment, three different suture materials, 4-0 Dacron, 4-0 Ethibond, and 4-0 Supramid ®, were tested. A total of 78 double loop suture units (26 with each material) were constructed, framed and placed under a tension of 1000 grams, and kept in a saline container. Serial measurements of the tensile strength were made at zero, one, two, three, five and eight weeks following construction of the sutures.

Figure 18:
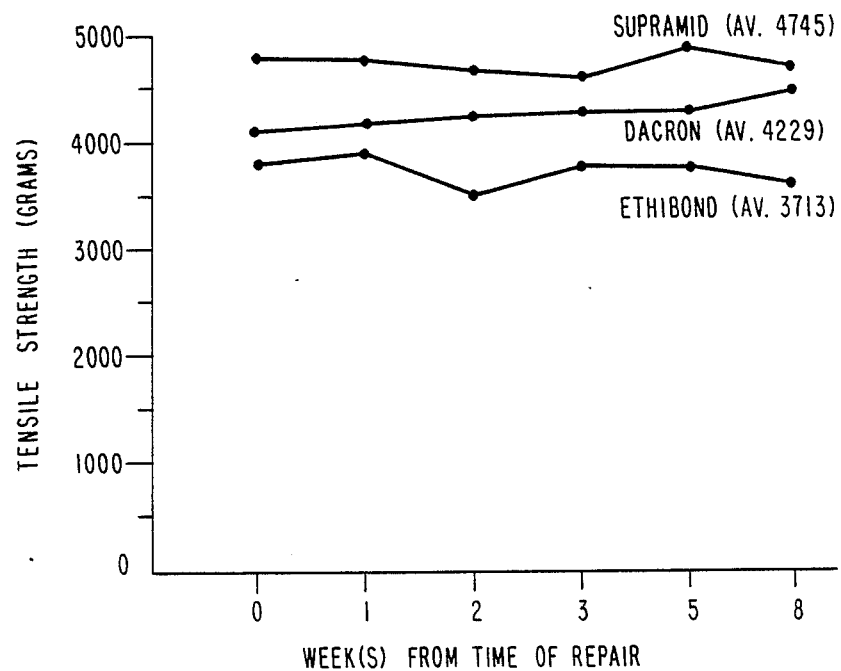
FIG. 18 is a graph depicting the results of the experimentation conducted with the assembly of FIG. 17.

With reference to Table 2 and FIG. 18, the average tensile strength of the double loop sutures (all 4-0) was 4229 grams with Dacron, 3713 with Ethibond, and 4745 grams with Supramid ®. Most of the ruptures during the test occurred at or near the knots although some occurred around the rings because of its sharp edges. All three suture materials maintained essentially the same strength throughout the test period of eight weeks.

The tensile strength of the tendon repair utilizing the double loop locking suture technique of the present invention of 4400 grams in Experiment 1 was similar to that of the double loop sutures (only) in Experiment 2 (4229 grams). Experiment 1 indicated that the weakest point of the tendon union is the suture area. Therefore, tensile strength of the tendon union should increase with the improvement in the suture strength.

As a result of the foregoing experimentation, Supramid ® showed the highest tensile strength and is available from S. Jackson Incorporated, Alexandria, VA.

The principle of repair of the double loop locking sutures in accordance with the present invention, as best understood, involves the transfer of longitudinal load or tension transmitted through the tendon juncture into a transverse compression force by the use of the double loop locking sutures. In other words, tension transmitted through the first and second tendons repaired with the present invention is transmitted through the square knots 33 (FIGS. 10 and 11) as an axial load to the transverse double loop locking sutures 15', 15' and 29', 29' where the force is converted into a transverse compression force. Since a pair of double loop locking sutures are formed in each tendon end through the transverse mid-axis of the tendon and exit the tendon end more or less symmetrically relative to a longitudinal bisecting plane 89 (FIG. 9A), the longitudinal load is thereby carried and uniformly distributed between the first and second locking sutures 15', 29' in each of the first and second tendons 10, 12. As a result of the extensive experimentation discussed above, the preferred material for the loop sutures is a nonabsorbable, multifilament, usually 4.0 and occasionally 3.0 or 5.0, Nylon (preferably Supramid ®) or polyester (preferably Dacron).

To avoid gap formation which is a well known cause of adhesion, the loop sutures must be pulled tightly in a longitudinal direction before tying. Since the double loop locking suture technique of the present invention advantageously avoids gap formation, the technique in conjunction with the preferred sutures mentioned above advantageously enables early active mobilization of the repaired tendons, preferably with the use of a splint, to enhance early intrinsic healing and reduce extrinsic adhesion.

It will be readily seen by one of ordinary skill in the art that the present invention fulfills all of the objects set forth above. After reading the foregoing specification, one of ordinary skill will be able to effect various changes, substitutions of equivalents and various other aspects of the invention as broadly disclosed herein. It is therefore intended that the protection granted hereon be limited only by the definition contained in the appended claims and equivalents thereof.

I claim:

1. A method of repairing tendons, comprising the steps of:
   (a) inserting a first needle attached to a first loop suture through a first tendon along its diametral axis leaving a loop of the first loop suture projecting laterally from the tendon;

(b) forming a plurality of superficial stitches across the volar half of the tendon along its circumference;

(c) passing the first needle through the loop, tightening the suture to form a first lockup suture and then inserting the first needle along the tendon fiber so that it passes under and across the first lockup suture and out through the end of the tendon;

(d) inserting a second needle attached to a second loop suture through the first tendon along its diametral axis and inwardly spaced from the first suture towards the tendon end, leaving a loop of the second loop suture projecting laterally from the tendon which second loop is diametrically opposed to the loop of the first suture;

(e) forming a plurality of superficial stitches in the volar half of the tendon along the circumference thereof;

(f) passing the second needle through the second loop, tightening the suture to form a second lockup suture and then inserting the second needle along the tendon fiber so that it passes under and across the second lockup suture and out through the end of the tendon spaced from the first loop suture exiting the tendon end;

(g) repeating steps (a)-(f) in a second tendon;

(h) tying loose ends of the first sutures together with a knot, tying loose ends of the second sutures together with a knot, tightening the knots to draw the ends of the tendons together and tying the knots; and (i) approximating the tendon juncture with other suture material.

2. The method of claim 1, wherein each loop suture is a nonabsorbable multifilament material.

3. The method of claim 2, wherein each first and second needle is a ⅜ circular needle.

4. The method of claim 1, wherein said tendon ends abut each other in end-to-end contact.

5. The method of claim 2, wherein said tendon ends abut each other in end-to-end contact.

6. The method of claim 1, wherein said tendons are of different diameters and the larger diameter tendon is split at its end into two halves terminating in an apex, wherein the first and second sutures extend longitudinally outward from the large diameter tendon through the apex of the split end, wherein the smaller diameter tendon is drawn between the split halves by tightening of said knots and wherein intussusception is completed by running sutures along split margins of the split ends such that the running sutures penetrate the smaller diameter tendon.

7. The method of claim 6, wherein each loop suture is a nonabsorbable multifilament material.

8. The method of claim 7, wherein each first and second needle is a half circular needle.

9. A tendon repair kit comprising a plurality of loop sutures each attached to a needle and instructions for repairing tendons with said looped sutures of said kit, said instructions comprising the steps of:

(a) inserting a first needle attached to a first loop suture through a first tendon along its diametral axis leaving a loop of the first loop suture projecting laterally from the tendon at the entrance point of the first needle;

(b) forming a plurality of superficial stitches in the volar half of the tendon along the circumference;

(c) passing the first needle through the loop, tightening the suture to form a first lockup suture and then inserting the first needle along the tendon fiber so that it passes under and across the first lockup suture and out through the end of the tendon;

(d) inserting a second needle attached to a second loop suture through the first tendon along its diametral axis and inwardly spaced from the first suture towards the tendon end, leaving a loop of the second loop suture projecting laterally from the tendon which second loop is diametrically opposed to the loop of the first suture;

(e) forming a plurality of superficial stitches in the volar half of the tendon along the circumference thereof;

(f) passing the second needle through the second loop laterally, tightening the suture to form a second lockup suture and then inserting the second needle along the tendon fiber so that it passes under and across the second lockup suture and out through the end of the tendon spaced from the first loop suture exiting the tendon end;

(g) repeating steps (a)-(f) in a second tendon;

(h) tying loose ends of the first sutures together with a knot, tying loose ends of the second sutures together with a knot, tightening the knots to draw the ends of the tendons together and tying the knots; and (i) approximating the tendon juncture with other suture material.

10. The kit of claim 9, wherein said instructions comprise the further steps of wherein said tendons are of different diameters and the larger diameter tendon is split at its end into two halves, wherein the first and second sutures extend longitudinally outward from the large diameter tendon through the apex of the split end, wherein the smaller diameter tendon is drawn between the split ends by tightening of said knots and wherein intussusception is completed by running sutures along split margins of the split ends such that the running sutures penetrate the smaller diameter tendon.

11. A method of inserting a tendon into bone, comprising the steps of:

(a) inserting a first needle attached to a first loop suture through a first tendon along its diametral axis leaving a loop of the first loop suture projecting laterally from the tendon;

(b) forming a plurality of superficial stitches across the volar half of the tendon along its circumference;

(c) passing the first needle through the loop, tightening the suture to form a first lockup suture and then inserting the first needle along the tendon fiber so that it passes under and across the first lockup suture and out through the end of the tendon;

(d) inserting a second needle attached to a second loop suture through the first tendon along its diametral axis and inwardly spaced from the first suture towards the tendon end, leaving a loop of the second loop suture projecting laterally from the tendon which second loop is diametrically opposed to the loop of the first suture;

(e) forming a plurality of superficial stitches in the volar half of the tendon along the circumference thereof;

(f) passing the second needle through the second loop, tightening the suture to form a second lockup suture and then inserting the second needle along the tendon fiber so that it passes under and across the second lockup suture and out through the end of the tendon spaced from the first loop suture exiting the tendon end; and (g) forming a cortical window in the bone and inserting the first and second needle through the cortical window; inserting the end of the tendon into the bone through the cortical window and securing the tendon therein with knots.

* * * * *